May 27, 1958 | W. E. LAMMERTS | Plant Pat. 1,711
ROSE PLANT
Filed Sept. 19, 1957
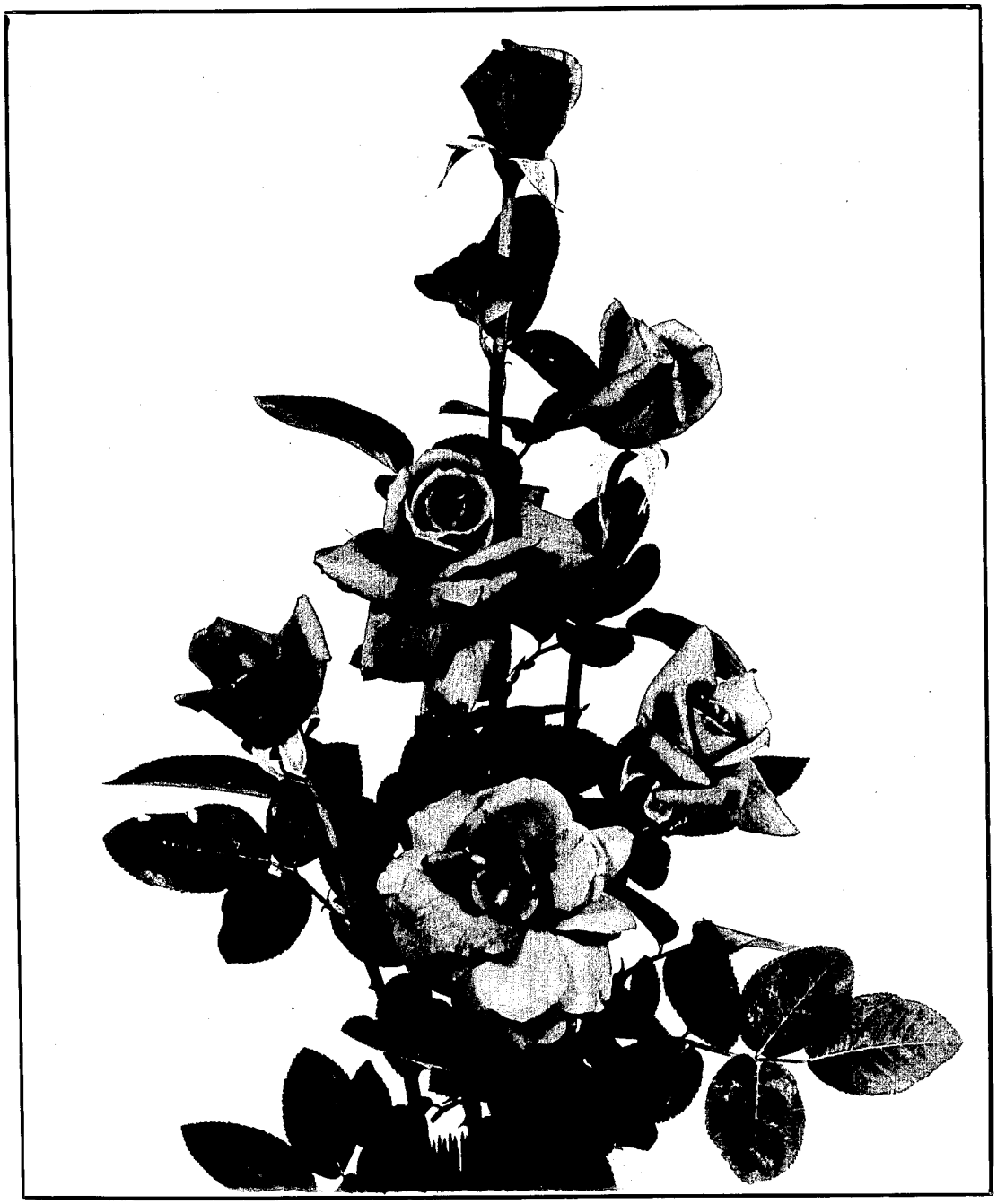
Inventor.
W. E. Lammerts
By: Robert Cobb
Attorneys.

United States Patent Office

Plant Pat. 1,711
Patented May 27, 1958

1,711

ROSE PLANT

Walter E. Lammerts, Livermore, Calif., assignor, by mesne assignments, to Germain's, Inc., Van Nuys, Calif., a corporation of California Application September 19, 1957, Serial No. 685,054

1 Claim. (Cl. 47—61)

The present invention relates to a new and distinct variety of rose plant of the hybrid tea class, which was originated by me by crossing the variety "Mirandy" (Plant Patent No. 632) with the variety "Grand Duchess Charlotte" (Plant Patent No. 774).

As the result of this breeding, I have produced a new rose variety which is distinctly different from both parents, as well as from all other varieties of its class of which I am aware, as evidenced by the following characteristics which are outstanding in the new variety and represent a new and unusual combination:

(1) The tall, vigorous and compact habit of plant growth;

(2) The habit of branching very freely from the base of the plant;

(3) The large and dark green glossy foliage;

(4) The long pointed buds which open readily even in cool weather into flowers of good form;

(5) The combination of both single and cluster flowering habit;

(6) The candelabra form of the flower clusters, with the individual blooms of the clusters, as well as the single flowers, being borne on long cutting stems suitable for cut flower use; and (7) The distinctive Rose Red general color tonality of the flowers.

Asexual reproduction of the new variety by budding, as performed by me at La Canada, California, shows that the foregoing characteristics and distinctions come true to form and are established and transmitted through succeeding propagations.

The accompanying drawing shows typical specimens of the vegetative growth and flowers of my new variety in different stages of development and as depicted in color.

The following is a detailed description of my new variety, with color terminology in accordance with the Horticultural Color Chart of the British Color Council, except where general color terms of ordinary dictionary significance are obvious:

Type: Hardy; tall; bush; outdoor; seedling; for garden decoration.

Class: Hybrid tea.

Breeding: Seedling.

*Seed parent.*—"Mirandy."

*Pollen parent.*—"Grand Duchess Charlotte."

Propagation: Holds its distinguishing characteristics through succeeding propagations by budding.

*Flower*

Locality where grown and observed: Livermore, California.

Flowers borne: Both singly and several to stem; in regular pyramidal clusters; on strong, long stems which, even in the clusters, are from 12 to 18 inches long.

Quantity of bloom: Abundant, outdoors.

Continuity: Continuous.

Fragrance: Strong. Nature—tea.

Bud:

*Peduncle.*—Long; medium caliper; erect; stiff; smooth; with numerous gland-tipped hairs of Magenta Rose, Plate 027/1. Color—Spinach Green, Plate 0960/3, tinged with anthocyanin pigment near Magenta Rose, Plate 027/1.

*Before calyx breaks.*—Size—large. Form—long; pointed; without foliaceous appendages on the surface of the bud; with slender, entire foliaceous parts extending beyond the tip of the bud equal to ¼ of its length; every other sepal (2 of the 5) having a very narrow lance-shaped appendage from ⅛ to ¼-inch long on each margin, with one of these appendaged sepals much longer than the others and having a serrated foliaceous tip from ⅜ to ½-inch long. Color—Purple Madder, Plate 1028.

*As calyx breaks.*—Color—Dahlia Purple, Plate 931, shading to chrysanthemum Crimson, Plate 824/2 near base of petal.

*As first petal opens.*—Size—medium large. Form—long; urn-shaped. Color: outside—Rose Red, Plate 724, tinged with Tyrian Purple, Plate 727 toward top of petal; inside—Chrysanthemum Crimson, Plate 824 at base, shading to Rose Red, Plate 724 near tip of petal.

*Opening.*—Opens up well, but is retarded by cold and wet weather.

Bloom:

*Size (when fully open).*—Medium large; from 4½ to 5 inches.

*Petalage.*—Double; from 35–40 petals; arranged regularly.

*Form.*—Full and high-centered at first, but becoming cupped; petals being at first very tightly rolled inward, but becoming loosely rolled outward at maturity.

Petals:

*Texture.*—Thick; soft. Inside—velvety. Outside—satiny.

*Shape.*—Outside—ovate, with apex having 2 notches. Intermediate—ovate, with apex having 1 or 2 notches. Inside—usually ovate, but with very irregular petaloids; usually with one notch.

This description of a newly opened flower was made from a rose grown outdoors in the month of June, at Livermore, California:

*Color.*—Outer petal: outside surface—Rose Red, Plate 724, shading to Tyrian Purple, Plate 727; inside surface—Tyrian Purple, Plate 727. Intermediate petal: outside surface—Rose Red, Plate 724; inside surface—Rose Red, plate 724, shading to Tyrian Purple, Plate 727. Inner petal: outside surface—Rose Red, Plate, 724; inside surface—Rose Red, Plate 724.

This description was made from a rose that was open for 3 days outdoors in the month of June, at Livermore, California:

*Color.*—Outer petal: outside surface—Tyrian Purple, Plate 727; inside surface—Tyrian Purple, Plate 727, shading to Peony Purple, Plate 729/1. Inner petal: outside surface—Tyrian Purple, Plate 727; inside surface—Tyrian Purple, Plate 727.

*General color effect.*—Newly opened flower—Rose Red, Plate 724. 3-days open—Tyrian Purple, Plate 727.

*Behaviour.*—Drop off cleanly; fading purple; tends to be more Tyrian Purple, Plate 727 as the result of cold and wet weather.

*Flower longevity.*—On bush in garden—3 days in June. Cut roses grown outdoors and kept at living-room temperatures—3 days in June.

*Reproductive organs*

Stamens: Many; arranged irregularly about pistils.
Filaments: Medium long; most with anthers. Color—Orient Red, Plate 819/1.
Anthers: Medium large; open at various times. Colors—Yellow Ochre, Plate 07/1.
Pollen: Abundant. Color—gold.
Pistils: Many.
Styles: Uneven; from short to medium length; thin; bunched; columnar.
Stigma: Color—Empire Yellow, Plate 603/2, with margin tinged with Orient Red, Plate 819/1.
Ovaries: All enclosed in calyx.
Hips: Globular; smooth; with walls thick and fleshy. Color—yellow.
Sepals: Permanent; moderately long; spear-shaped; recurved. Color: inside—Lavender Green, Plate 000761/1; outside—Willow Green, Plate 00862.
Seeds: Few; medium large.

*Plant*

Foliage:

*Leaves.*—Compound of 5–7 leaflets; abundant; very large; heavy; glossy.

*Leaflets.* — shape — oval. Apex — acute. Base — round. Margin—simply serrate.

*Color.*—Mature: upper surface—from Spinach Green, Plate 0960 to Spinach Green, Plate 0960/1; under surface—Lavender Green, Plate 000761/1. Young: upper surface—from Spinach Green, Plate 0960/2 to Spinach Green, Plate 0960/3, heavily tinged with anthocyanin; under surface—Lavender Green, Plate 00761/1, heavily tinged with anthocyanin.

*Rachis (the supporting stem of the compound leaf.*—Upper side—smooth; grooved. Under side—sparsely prickly.

*Stipules.*—Medium long; narrow; with medium long points turning out at an angle of more than 45°; recurved toward stem.

*Disease resistance.*—Resistance to mildew and blackspot, as compared with other varieties grown under comparable cultural conditions at Livermore, California.

Growth:

*Habit.*—Upright; compact, but branching well from base.

*Growth.*—Free; vigorous.

*Canes.*—Heavy.

*Main stems.*—Color—dull green, tinged with bronze. Thorns—many; long; hooked downward; with long, narrow base. Prickles—few; color—bronze. Hairs—few; color—red gland-tipped.

*Branches.*—Color—dull green, tinged with bronze. Thorns—many; long; hooked downward; with long, narrow base. Prickles—few; color—reddish. Hairs—few; color—reddish gland-tipped.

*New shoots.* — Color — grey-green, tinged with bronze. Thorns—many; long; hooked downward; with long, narrow base. Prickles—few; color — reddish. Hairs — few; color — reddish gland-tipped.

I claim:

A new and distinct variety of rose plant of the hybrid tea class, substantially as herein shown and described, characterized particularly as to novelty by its tall, vigorous and compact habit of plant growth, its habit of branching very freely from the base of the plant, its large and glossy dark green foliage, its long, pointed buds which open readily even in cool weather into flowers of good form, its habit of flowering both singly and in clusters of candelabra form, with both the single and cluster flowers borne on long stems suitable for cut flower use, and the distinctive Rose Red general color tonality of its flowers.

No references cited.